(12) United States Patent
Zadeh

(10) Patent No.: US 11,723,702 B2
(45) Date of Patent: Aug. 15, 2023

(54) MODULAR BONE SCREW FOR SURGICAL FIXATION TO BONE

(71) Applicant: Homayoun H. Zadeh, Woodland Hills, CA (US)

(72) Inventor: Homayoun H. Zadeh, Woodland Hills, CA (US)

(*) Notice: Subject to any disclaimer, the term of this patent is extended or adjusted under 35 U.S.C. 154(b) by 0 days.

(21) Appl. No.: 17/347,239

(22) Filed: Jun. 14, 2021

(65) Prior Publication Data

US 2022/0104857 A1 Apr. 7, 2022

Related U.S. Application Data

(63) Continuation of application No. 16/438,082, filed on Jun. 11, 2019, now Pat. No. 11,033,309, which is a continuation of application No. 15/279,426, filed on Sep. 28, 2016, now Pat. No. 10,357,296.

(60) Provisional application No. 62/234,008, filed on Sep. 28, 2015.

(51) Int. Cl.
| | | |
|---|---|---|
| *A61B 17/86* | (2006.01) | |
| *A61C 8/00* | (2006.01) | |
| *A61B 17/04* | (2006.01) | |
| *A61F 2/08* | (2006.01) | |

(52) U.S. Cl.
CPC ...... *A61B 17/8605* (2013.01); *A61B 17/0401* (2013.01); *A61B 17/863* (2013.01); *A61B 17/8685* (2013.01); *A61C 8/0025* (2013.01); *A61C 8/0096* (2013.01); *A61F 2/0811* (2013.01); *A61B 2017/044* (2013.01); *A61B 2017/0414* (2013.01); *A61B 2017/0464* (2013.01); *A61C 8/008* (2013.01); *A61C 8/0022* (2013.01); *A61F 2002/0829* (2013.01); *A61F 2002/0852* (2013.01); *A61F 2002/0888* (2013.01)

(58) Field of Classification Search
CPC ... A61C 8/0075; A61C 8/0028; A61C 8/0025; A61C 8/0024; A61C 8/0022; A61F 2002/0888; A61F 2002/0852; A61F 2002/0829; A61F 2/0811; A61B 2017/0464; A61B 2017/044; A61B 2017/0414; A61B 17/8685; A61B 17/8605; A61B 17/863; A61B 17/0401
See application file for complete search history.

(56) References Cited

U.S. PATENT DOCUMENTS

| | | | |
|---|---|---|---|
| 5,108,399 A | 4/1992 | Eitenmuller et al. | |
| 5,964,768 A | 10/1999 | Huebner | |
| 6,139,550 A | 10/2000 | Michelson | |
| 7,325,470 B2 | 2/2008 | Kay et al. | |

(Continued)

*Primary Examiner* — Nicholas D Lucchesi
(74) *Attorney, Agent, or Firm* — Kurt T. Mulville; VLP Law Group LLP

(57) ABSTRACT

The invention discloses a modular surgical bone screw assembly having a threaded base portion and a screw head adapted to attach a variety of structures to bone. The features of the screw include a modular design for the assembly that separates the function of anchorage to the recipient bone to one of the modules of the device (threaded portion) from the other function of attaching another element (such as bone block, membrane, orthodontic wires, elastics etc) to a second module (the screw head). The design also allows the head to be exchanged after the implant has been placed.

8 Claims, 7 Drawing Sheets

(56) References Cited

U.S. PATENT DOCUMENTS

| | | | |
|---|---|---|---|
| 8,361,129 B2* | 1/2013 | Chao | A61B 17/7037 |
| | | | 606/264 |
| 8,506,608 B2* | 8/2013 | Cerynik | A61B 17/72 |
| | | | 606/76 |
| 8,652,183 B1* | 2/2014 | Truman | A61B 17/8605 |
| | | | 606/305 |
| 8,740,955 B2 | 6/2014 | Bottlang et al. | |
| 8,828,067 B2 | 9/2014 | Tipirneni et al. | |
| 10,357,296 B2* | 7/2019 | Zadeh | A61B 17/0401 |
| 11,291,484 B2* | 4/2022 | Chan | B23G 1/02 |
| 2003/0083660 A1 | 5/2003 | Orbay | |
| 2010/0023064 A1 | 1/2010 | Brunger et al. | |
| 2010/0145394 A1 | 6/2010 | Harvey et al. | |
| 2012/0029569 A1 | 2/2012 | Iott et al. | |
| 2013/0053901 A1 | 2/2013 | Cormier et al. | |
| 2013/0079826 A1 | 3/2013 | Simonson | |
| 2013/0218213 A1 | 8/2013 | Lemoine | |
| 2013/0253594 A1 | 9/2013 | Zucherman et al. | |
| 2014/0336709 A1 | 11/2014 | Widano et al. | |
| 2016/0242820 A1 | 8/2016 | Shipple et al. | |
| 2017/0007306 A1 | 1/2017 | Werner | |
| 2017/0119445 A1 | 5/2017 | Lemoine | |
| 2018/0000528 A1 | 1/2018 | Austin et al. | |
| 2018/0028236 A1 | 2/2018 | Ziemek et al. | |
| 2018/0028245 A1 | 2/2018 | Ziemek et al. | |

\* cited by examiner

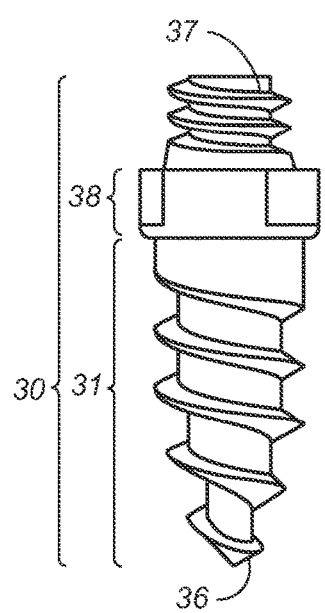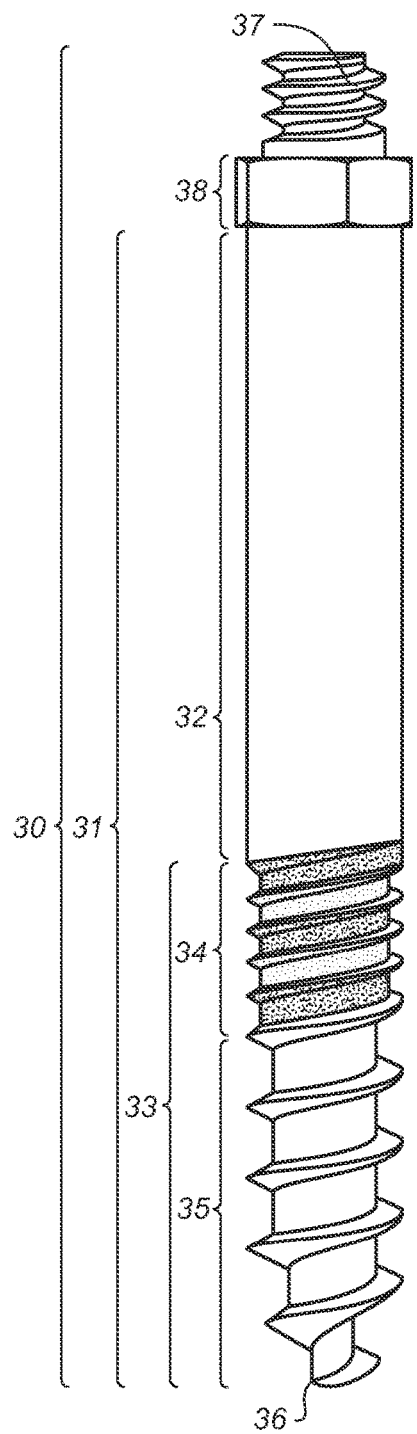
*FIG. 3A*  *FIG. 3B*  *FIG. 3C*

MODULAR BONE SCREW FOR SURGICAL FIXATION TO BONE

CROSS REFERENCE TO RELATED APPLICATIONS

This application is a continuation of U.S. patent application Ser. No. 16/438,082, filed Jun. 11, 2019, which is a continuation of U.S. patent application Ser. No. 15/279,426, filed Sep. 28, 2016, now U.S. Pat. No. 10,357,296, issued Jul. 23, 2019, which claims priority to U.S. Provisional application Ser. No. 62/234,008, filed Sep. 28, 2015. The priority of these applications is expressly claimed, and the Provisional Application and the Non-provisional Applications are hereby incorporated by reference in their entireties.

FIELD OF THE ART

The present invention is in the field of surgical bone screws used for attachment of structure or fixation of bone during surgery.

BACKGROUND

A wide variety of surgical applications require the placement of surgical screws in bone tissue. Some procedures use bone tissue as an attachment point for other devices such as titanium mesh, orthodontic anchors, resorbable or nonresorbable membranes. Other procedures require attachment of bone graft to host bone, such as the fixation of a bone block or graft or stabilization of a fracture. It is often necessary to stabilize soft tissues such as mucosa, skin, muscle or tendon, in which case bone provides a stable anchorage onto which soft tissues can be attached. Creating a stable and secure attachment point is difficult because the bone tissue must support large mechanical forces and the attachment of synthetic or graft structures to bone places enormous stress on both the bone and the attachment device at the point of attachment or fixation.

Traditionally, surgical screws have been used to attach a desired structure to bone. The desired attachment structure may be another piece of bone, a graft or synthetic prosthetic, a mesh or biocompatible implant, or a dental prosthetic. Ordinary surgical screws are attached to bone in the same manner that ordinary hardware screws employ. Using a driver, such as a screwdriver, the user contacts the head of the screw with an engaging fixture at the distal end of the driver and manually rotates the threaded portion of the screw until the screw penetrates the target site at a selected point and the attachment by the screw secures the selected attachment structure at the desired attachment point. The problem with current surgical screws is that the graphs or devices, which are typically being anchored to bone at the target site, interfere with visualization of underlying bone at the target site and can interfere with the proper placement of the screw into bone. Also, many surgical procedures, and particularly dental procedures, require precise placement of bone in confined spaces with delicate bone and tissue structures and difficult geometries.

Moreover, anytime screws are used in surgical applications, it is particularly important that the screws be placed securely and stably and that any attached structure is precisely placed and completely secured to the bone at the target site and without damaging the bone that provides support for the attached structure. The task is particularly challenging with the limited fields of view inherent in dental applications, such as when placing an anchor, where visualization of the attachment of the fixture takes place between teeth and requires careful and stable securing of the structure to the jaw bone.

Thus, the existing surgical practices and apparatus have at least the following drawbacks: 1) the attachment structure must be held in place while the threaded portion of the screw is drilled into the bone under limited visibility; 2) the placement can be inaccurate and often damage the bone when the underlying bone is visually blocked by the screw, the attachment structure, or both; 3) driving a screw through surrounding membranes can cause the membrane to rotate and the attachment between the driver and the screw is generally unstable.

Accordingly, a need exists for an improved bone screw design that enhances a surgeon's ability to more carefully control the process of driving a screw into bone and improve the application of the attachment structure to bone while enhancing the surgeons' visualization of the procedure.

SUMMARY OF INVENTION

The present invention is surgical devices and methods for a surgery wherein a structure is attached to bone. Specifically, modular (one and two-piece) bone screws are designed as an alternative to conventional bone screws commonly used today. In one embodiment, two-piece assemblies allow a threaded based portion having an elongated shaft to first be anchored in bone at an optimal height, configuration, and location, followed by attachment of a head piece in the form of a cap that can have a variety of configurations depending on the surgical application, including fixation of bone blocks, fixation of barrier membranes, stabilization of titanium mesh, securing prosthetic implants, space provision as tenting cap above the screw, attachment of dental prosthetics, as well as for orthodontic anchorage. The applicable the head piece may also feature additional structures that function for attachment of tissue or bone to the screw assembly, including one or more eyelets or grooves formed in the cap for attachment of sutures to the surrounding membrane or overlying flap.

In another embodiment, a unitary screw is provided as one-piece assembly of the shaft and had integrally formed in a single structure that combines the operative structures of the two-piece embodiment with similar enhanced anchoring stability, tissue fixation, and the compatibility with a driver.

Surgical procedures that take advantage of the improved properties of the screw assemblies of the invention include attachment of bone grafts harvested from donor sites, placement of bone blocks, space provision as tenting screws and caps for guided bone regeneration (GBR), fixation of fractures, preparation of anchors to place dental implants and other anchorage devices, fixation of sutures or wires and essentially, any surgical operation on bone requiring placement of screws—particularly where the placement of a screw acts as an anchor, is followed by a removable placement of a head piece having a removable cap with a specific function and is performed under limited visibility.

DESCRIPTION OF THE FIGURES

FIGS. 3A-3C are embodiments of a modular screw comprised of a shaft portion and a head region having a threaded post at the most proximal point for releasable attachment of a variety of caps. The embodiment of FIG. 3A has a minimal height of the non-threaded portion, suitable for membrane fixation, while the embodiment of FIGS. 3B and 3C illustrate non-threaded portions of variable height depending on the surgical environment.

DETAILED DESCRIPTION OF INVENTION

Figure 1:
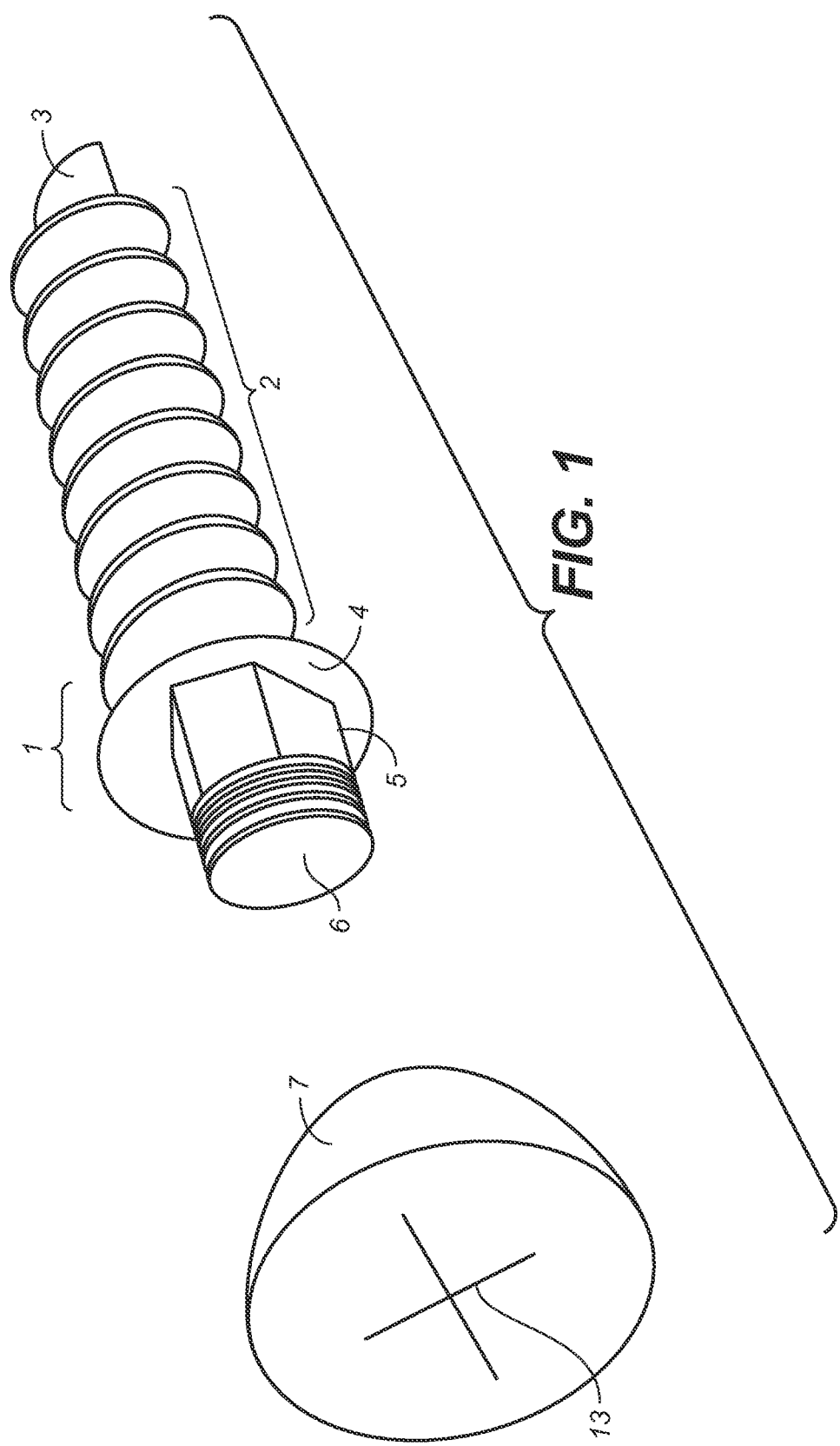
FIG. 1 is a modular assembly showing the threaded base portion and an example of a head attachment, in this case a healing abutment that is releasably affixed to the proximal portion of the shaft and is an example of a screw assembly used in dental implants.

The screw assembly for bone surgery according to the present invention provides a modular assembly comprised of a threaded screw base piece having a distal threaded portion terminating in a tip and a proximal portion for affixation to a screw head. The screw also be comprised of a non-threaded portion along an axial length thereof. The most proximal portion of the screw may also have means for attachment of a cap, engaging a driver, or an engaging means preferably recessed into the headpiece. In the alternative embodiment, the means for engaging the driver is disposed in the upper surface of the cap. In the multi-piece assembly embodiments, the cap is designed to engage both the driver at the upper portion, typically through a hex fixture, while the bottom portion has an internal thread to engage the proximal portion of the screw or screw base. Depending on the purpose of the cap, various configurations for the cap of the screw assembly can be attached or mounted to a corresponding threaded portion, such as the threaded post, at the proximal end of the screw base. Accordingly, when initially placed, the screw has a low profile for stability in the target bone and enhanced visualization while being fixed at the target site. Secure fixation of the shaft portion of the screw assembly is followed by releasable attachment of the selected cap, and optionally securing surrounding membrane tissue to the cap, in either of an integrated embodiment of the screw assembly or as a modular two-piece cap and shaft pairing.

The modular screw assemblies of the invention can be provided as a kit having differently sized screw assemblies and including drivers and other fixtures for organization, sterilization, and storage of the screw assemblies and related devices.

The kits typically include the following items for use in placement of the screw assemblies: an autoclavable tray, a screw assembly and cap organizer wheel, a swivel driver handle, at least one swivel bone screw driver, at least one swivel 0.05" hex driver, a latch-type bone screw driver, a latch-type 0.05" hex driver, a counter-sink drill, a Pilot drill, a membrane punch, and forceps. The kit includes a variety of modular screw assemblies having different diameters (typically approximately 1.2, 1.5 and 1.8 mm) and varying lengths (ranging from approximately 4 to 14 mm).

Additionally, at least are 4 types of caps are provided as part of the kits including the tenting caps, block fixation caps, membrane fixation caps, and orthodontic cap.

The kits of the invention will have at least the following applications: 1) fixation of bone blocks (autogenous, allogenic or alloplastic) to recipient bone; 2) fixation of barrier membranes, titanium mesh, or resorbable mesh; 3) placement of tenting screws; 4) placement of orthodontic anchors, 5) attachment of soft tissues such as mucosa, muscle, tendon or skin, and 5) for experimental purposes in animals or human, where biofilm will be cultivated in vitro on one or both pieces prior to installation in situ. Such models can be applied in an experimental model of biofilm-mediated peri-implantitis.

The threaded portion of the shaft of the screw assembly can take advantage of a variety of known thread designs, including but not limited to V-thread, square thread, rounded thread, buttress thread, reverse buttress thread, etc. The threads may have various self-tapping macro-design features and may be made with a variety of different pitch formats and sizes in order to match with the recipient bone, as well as purpose of the screw installation. For example, macrothreads having larger pitch at terminal portion of the screw may be combined with microthreads in the penultimate portion of the screw in order to provide improved stability and minimize the possibility of peri-implant bone loss during function These materials can be made of a variety of biocompatible resorbable or non-resorbable material, including but not limited to Titanium (commercially pure or titanium alloy), stainless steel, zirconium, peek plastic, Polytetraflouroethylene (PTFE), polypropylene, Poly(lactic acid), polylactide (PLA), Polyglycolide or Polyglycolic acid (PGA), Polycaprolactone (PCL), polyurethane, hydroxyapatite (HA), tri-calcium phosphate (TCP) or combination of these and other polymers.

The threaded portion of the screw shaft will be installed into bone preferably using a geometric structure on the head region of the screw shaft that performs the function of engaging a driver having a meeting fixture that are joined together in conforming engagement to allow the surgeon to rotate the driver, which in turn rotates the shaft, around the long axis of the length of the shaft. In this aspect, use of the specially designed devices of the invention results in an improved operation of driving a screw into a target site in what is essentially a conventional operation comprised of using the driver to rotate the screw assembly shaft, applying pressure at the distal tip of the shaft to drive the shaft into the supporting bone. An example of such a combined mechanism is a multi-sided geometry, such as hexagon or square, at the hex portion of the shaft disposed superior to the non-threaded portion and inferior to the threaded post.

An internal hexagonal or square driver may be used to engage the hexagonal portion of the threaded shaft portion to drive the shaft into bone to form a fixed base structure for attachment of any structure or to form an anchor such as during the installation of a dental implant. This configuration of having the proximal portion of the implant act as the male and the driver internal component as the female is critical for stabilization of the implant during insertion. The most proximal portion of the screw shaft may be further comprised of a retentive element, such as threading, to help in releasably attaching the cap. The cap has internal threaded and complementary retentive elements formed to engage the threaded post for attachment to the screw shaft. As described herein, the shaft preferably also has a geometric element (slot, internal hexagon, internal square, etc) on the exterior and distal to the threaded portion so that a driver can engage the screw shaft at a point proximal to the threaded portions.

In a preferred embodiment, the threaded portion is comprised of separate threaded regions having differing pitches and depths. In one embodiment, the screw comprises at least two different pitches and two different depths that are preferably contiguous and disposed between the non-threaded portion and the tip. Accordingly, considering the structural orientation of the screw assembly from proximal to distal, the screw base is comprised of a threaded region, preferably consisting of a post, to receive a selected cap or screw head, a hex region to match a complementary-shaped fixture on the shape of a distal end of a driver that is to engage the screw portion to accomplish rotation necessary for screw insertion, a non-threaded region, a first threaded region, preferably having a smaller pitch and/or depth than a separate, second threaded region having a larger pitch and/or depth, and a distal tip.

Additional components such as an O-ring or concentric desk may be utilized when the screw is used for stabilization of a barrier membrane or mesh. Such O-ring or other barrier will be placed onto the screw proximal to the threaded portion(s) prior to placement of the membrane or mesh and aids to stabilize the membrane/mesh against the screw head. In the absence of such a structure, the membrane/mesh may slide down and move down on the bone screw shank.

As noted above, the screw head or cap may be fabricated with a variety of different designs for different surgical applications. Examples of different heads include: tapered heads for installation of block grafts; small flat heads (1.5 to 3 mm) for fixation of barrier membranes or titanium mesh; large flat head (2.5 to 5 mm) for application as tenting screws, which are used to create a tent-pole effect around particulate graft material in order to provide stability and maintain the space in guided bone regeneration; internal channels inside the head for orthodontic wires, which are used for temporary anchorage during orthodontic therapy; and a hooks on the screw head for orthodontic elastics, which are used for temporary anchorage during orthodontic therapy. As described below, particularly with respect to the embodiments of FIGS. 4A-4C, upon completion of the surgical screw assembly, any one of the variety of caps, including at least a tenting cap, a bone block fixation cap, a membrane fixation cap, or an unitary modular cap, is releasably placed at the most proximal portion of the screw.

A variety of different overall diameters and lengths of the screw may readily be fabricated. Different mechanisms to vary the length of the implant are to 1) vary the length of the threaded portion or any of a plurality of threaded portions were present, 2) vary the length of the non-threaded portion and/or 3) vary the length of the driver attachment structure or the overall height of the threaded post.

Referring to FIG. 1, a screw assembly 1 is shown having a threaded base portion consisting of a threaded shaft 2 having series of threads in a rotation about the circumference of the shaft 2 and terminating in a pointed distal tip 3. The threads of this embodiment are a self-tapping design made from materials and having dimensions ordinarily used in surgical screws. The threaded portion may have an overall length approximating 3 mm, a spline diameter of proximally one millimeter and an overall total diameter including the threads of approximately 1.2, 1.5 mm or 1.8 mm. The upper most portion of the threaded region 2 terminates in a disk 4 or other abutment that controls the depth at which threaded portion 2 may enter bone tissue. In the embodiment of FIG. 1, the disk 4 is a concentric circle surrounding the shaft of the threaded portion 2, although any structure acting as a functional stop to prevent further rotation of the screw upon entry of maximum depth into tissue may be used. Typically, the disk 4 has a diameter of approximately 1.5 mm and acts as a seat for engagement of the healing abutment at the proximal end of the screw assembly 1. Adjacent to the disk portion 4 is a means for engaging a driver during rotational manipulation of the screw during placement in bone. In the embodiment of FIG. 1, the means for engaging a driver is a hex feature 5 is a hex bolt sized and shaped to fit with a complementary hex feature typically located at the distal end of a handheld driver in use, the hex feature 5 on the screw assembly 1 is sized and shaped for engaging the corresponding hex on the driver that allows the user to manually, or through a power driven mechanism, rotate the entire threaded base portion of the screw assembly 1 to drive the unit into bone. In the embodiment of FIG. 1, an O-ring is illustrated. The O-ring is used when a barrier membrane or titanium mesh or other forms of mesh are used in order to maintain their position in a stable location immediately below the screw head.

Referring to FIG. 1, a screw assembly 1 is shown having a threaded base portion consisting of a threaded shaft 2 having series of threads in a rotation about the circumference of the shaft 2 and terminating in a pointed distal tip 3. The threads of this embodiment are a self-tapping design made from materials and having dimensions ordinarily used in surgical screws. The threaded portion may have an overall length approximating 3 mm, a spline diameter of proximally one millimeter and an overall total diameter including the threads of approximately 1.2-1.5 mm. The upper most portion of the threaded region 2 terminates in a disk 4 or O-ring or other abutment that controls the depth at which threaded portion 2 may enter bone tissue and acts as a stop for attachment of the healing abutment 7. In the embodiment of FIG. 1, the disk 4 is a concentric circle surrounding the shaft of the threaded portion 2, although any structure acting as a functional stop to prevent further rotation of the screw shaft 2 upon entry of maximum depth into bone or tissue may be used. Typically, the disk 4 has a diameter of approximately 1.5 mm and acts as a seat for engagement of the healing abutment 7 at the proximal end of the screw assembly 1. Adjacent to the disk portion 4 and disposed between the threaded portion of the shaft two and the disk 4 is a geometric fixture for engaging a driver during rotational manipulation of the screw during placement in bone. In the embodiment of FIG. 1, the means for engaging a driver is a hex feature 5, such as a hex bolt sized and shaped to fit with the complementary hex feature located at the distal end of the driver (not shown), which usually is a handheld driver having the ability to pivot at a point along the shaft 2 for angular attachment to the engaging means such as the hex portion 5. In use, the hex portion 5 of the screw assembly 1 is sized and shaped for engaging the corresponding hex on the driver that allows the user to manually, or through a power driven mechanism, rotate the entire threaded 2 forming the base portion of the screw assembly 1 to drive the unit into target bone.

In the embodiment of FIG. 1, the most proximal portion of the shaft 2 of the screw assembly 1 may also be comprised of means for retaining the healing abutment 7 or cap atop the screw assembly 1. In the embodiment of FIG. 1, the retaining means is a threaded post 6 at the head region of the screw assembly 1 that engages complementary threads located on the interior of the healing abutment 7 or any selected cap. Accordingly, the mating engagement of the threaded post 6 of the screw assembly 1 and the threaded interior of the healing abutment 7 or cap comprise the structure that removably retains the abutment or cap feature selected by the surgeon based on the needs of the procedure. O Once the completed screw assembly 1 is assembled and in place, the screw assembly 1 can also be considered to include the abutment 7 or cap when releasably attached to the shaft portion 2 of the screw assembly 1. (See FIGS. 2A-2E, 4A-4C).

In the embodiment of FIG. 1, the threaded post 6 is the most proximal structure of the base portion of the screw assembly 1 and is intended to engage the complimentary threaded portion of the screw head or cap. The threaded portion of the shaft 2 is self-tapping based on the pointed structure of the tip 3 and the orientation of the threads along the threaded portion of the shaft 2. The spline diameter is typically approximately 1 mm and the total diameter of the threaded shaft portion 2, including the maximum depth of the individual threads, is approximately 1.2 mm. The hex portion 5 may have an overall length of approximately 0.75 mm and a diameter of 1.0 mm. The abutment, of the disk 4 shown in FIG. 1, preferably has a diameter of approximately 1.5 mm.

Figure 2A:
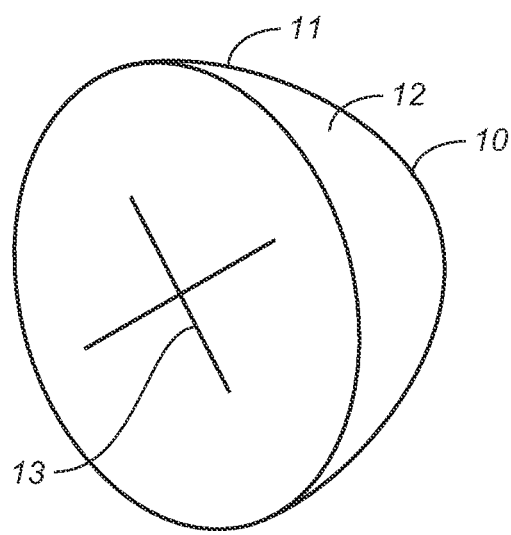
FIGS. 2A-2E are embodiments of the head unit of the screw assembly, used for membrane fixation, as tenting screws, for block graft fixation, as orthodontic anchorage, as well as a hook to assist with engagement of an elastic used in orthodontics.

Referring to FIGS. 2A-2E, the screw head of FIG. 2A is similar to the healing abutment 7 typically used in dental implant surgery for temporary placement during healing before a permanent replacement tooth is attached but also has the same general size and configuration of a block graft cap. The healing abutment 7 has a base portion 10 interior to which (not shown) is the receiving threaded portion described above that is adapted to engage and releasably attach the corresponding fixture, such as threaded post 6 on the most proximal end of the screw assembly 1. The base portion 10 also abuts and engages the disk 4 about the periphery thereof when rotated onto the screw assembly 1 following secure placement at the target site. The base portion 10 typically has a diameter and shape sized to conformly engage with the disk 4 upon placement. The average diameter of the base portion 10 approximates 1.5 mm. The healing abutment 7 has a tapered edge 12, typically approximating 2.0 mm in length (or axial height when releasably attached to the screw assembly 1, and may feature in a soft planar top portion 11 that forms a low profile screw head cap for attachment to the threaded post 6 of the screw assembly 1 and having an overall profile at the most proximal portion of approximately 3.0 mm. The upper surface of the healing abutment 7 screw head of the embodiment of FIG. 2A may also include a fixture for rotating the screw head unit such as intersecting slots 13 that permit secure attachment to the threaded post 6 of the screw assembly 1 base.

Figure 2B:
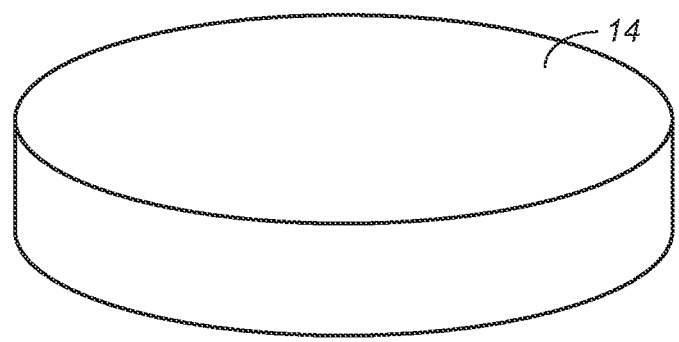

Referring to FIG. 2B, a very low profile tenting cap 14 is shown that may attach to either the threaded post 6 of the screw assembly 1 directly, or may cover any of the other screw and cap embodiments disclosed herein. For use together with the embodiment of 2A, the tenting screw cap 14 of FIG. 2B would be placed on top of the healing abutment 7 in order to provide s separate covering layer. This structure may have a minimal overall height and may eliminate the need for an internal threaded structure and may simply snap into place on top of any of the other healing abutment seven structures or any of the other variety of caps described herein. Alternatively, the tenting screw cap 14 of the FIG. 2B could be individually attached and would feature a structure on the lower, inferior surface thereof (not shown) to engage the most proximal point of the screw assembly 1 at the most proximal point thereof.

Figure 2C:
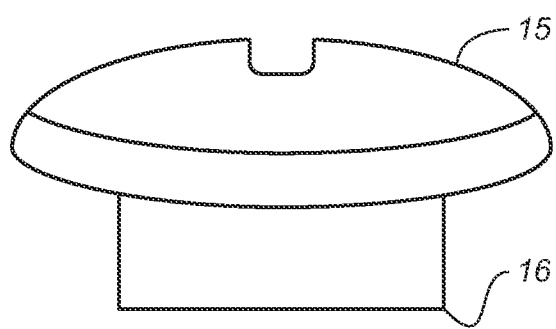

Referring to the embodiment of FIG. 2C, a cap in the form of a dome-shaped membrane cap 15 is provided for attachment of an additional attachment structure such as a titanium mesh or GBR membrane. In this embodiment, the screw cap 15 is attached to the threaded post 6, either by rotation using threaded retention means as described above, or by a simple snap fixture (not shown). The added function of the screw cap of embodiment of FIG. 2C is the ability to engage an additional attachment structure, preferably by a simple snap feature about the exterior of the screw cap. In a typical anchor-attachment function, the dome shaped portion of the upper most dimension of the screw cap 15 of FIG. 2C is larger than an inner diameter 16 and so secures a mesh or membrane attachment by conventional means. Contrary to the embodiment of FIG. 2A, the screw cap of FIG. 2C is specifically designed to have a raised profile such that an smaller inner diameter 16, and the difference between the outer diameter of the cap 15 and the inner diameter 16 provides a working space for secures attachment of the separate attachment structure, such as a suture, loop, or mesh.

Turning to the embodiment of Figure of 2D, a wire cap specifically designed for attachment of orthodontic wires is provided having both a tapered region 16a to raise the elevation of the cap and to serve as support for a wire attachment means 19 that may be comprised of a slot 17 and a through-hole 18. Each of the slot 17 and the through-hole 18 provide alternate attachment points for orthodontic wires. As will be appreciated by one of skill in the art, other structures can provide means for securely attaching wires and to comprise the wire attachment means which are preferably located at the uppermost (most proximal) point of the screw head 16a. In addition to slotted features 17 or holes 18, a simple post or crimping feature can be provided that securely attaches a wire to the wire cap or screw head 16a. As revealed in FIG. 2D, the overall height of the screw head 16a may be varied by adjusting either the height of the body of the screw head 16a or by altering the configuration of the wire attachment means to increase the total height above the base portion of the screw assembly 1.

Figure 2D:
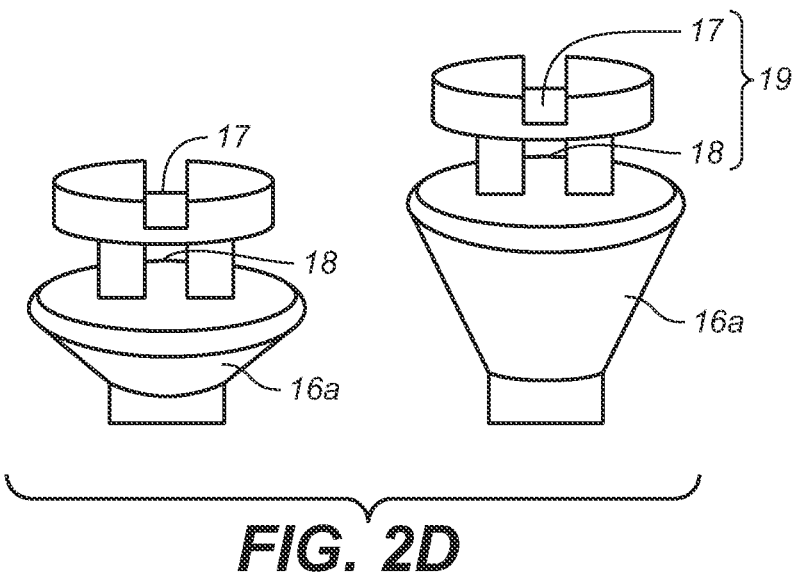
Figure 2E:
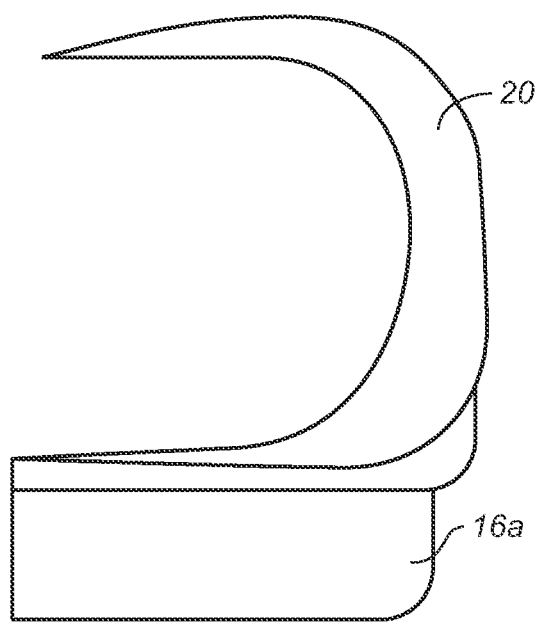

The embodiment of FIG. 2D typically includes a screw head configuration such that the positioning of the wire cap 16a relative to the wire is fixed and may be placed intermediate or at a terminal end of the wire. Additionally, as in the embodiment of FIG. 2E, the screw head 16a may allow for a sliding engagement of that attachment relative to the position of the wire cap. In the embodiment of FIG. 2E, a simple C-shaped hook 20 is formed in the top portion of the cap so that a separate attachment expedient may simply and easily be attached and removed, or may slide along its length through the opening in the hook portion 20.

Referring to FIG. 3A, the lowest profile embodiment of the modular screw assembly 30 is advantageously used for membrane fixation and does not have a non-threaded portion of the shaft 31 of substantial length. (Compare FIGS. 3B and 3C at reference 32). The membrane fixation screw assembly 30 of the embodiment of FIG. 3A, features the same properties of insertion and retention as the embodiments of the FIGS. 3B and 3C but in a lower profile designed for membrane fixation in that the reduced length of both the non-threaded 32 and threaded portions 35 result in the requirement that fewer turns of the driver are needed to secure the membrane fixation screw 30 in place.

Referring to FIGS. 3B-3C, the modular screw 30 is composed of shaft portion 31 and the head, which is comprised of the threaded post 37 and the driver engagement structure such as a hex bolt 38. The shaft 31 is comprised of a threaded portion 33 and a non-threaded portions 32. The overall length of the threaded portion 33 is designed for bone anchorage. The overall length of the threaded portion 33 is preferably comprised of a plurality of individual threaded regions 34, 35 of lesser length and containing differently threaded regions. The individual threaded regions 34, 35 are described as comprising macrothreads 35 and microthreads 34, wherein the macrothreads 35 have larger and deeper pitch, while the microthreads 34 have thread pitches that are closer together and more shallow. The microthreads 34 are designed to increase the overall, primary stability of the screw assembly 1, while reducing stress to bone during placement and that can lead to peri-implant crestal bone loss and eventual loss of function. As is apparent from FIGS. 3A-3C, the non-threaded portion 32 of the modular screw 30 is variable in height in order to meet the need for different augmentation heights.

As in the embodiment of FIG. 1, the head portion is comprised of a geometrically shaped structure 38 for engaging the distal end of a driver, such as a hex region 38 that is sized and configured to mate with the driver in complementary fashion. Typically, the hex receptacle of the driver is an internal fixture disposed at the most distal end of the driver and that matches size and the configuration of the geometric structure 38 such that rotational action of the driver results in the progressive insertion of the modular screw 30 into bone. In other embodiments, the hexagonal shape of the geometric structure 38 may be replaced by other geometric shapes onto which the driver may engage, including, for example, triangular, square, ovoid or star-shaped.

The head region may also be comprised of a variety of differently structured means for attaching or retaining a healing abutment or cap. While in the embodiments described above, the retentive elements primarily of a threaded post 37 with complementary threads on the internal portion of the various caps, a number of other attachment expedients are capable of facilitating releasable attachment of the cap to the proximal most portion of the modular screw 30. Other forms of retention may include an undercut (not shown) onto which the cap can snap into stable connection. In other embodiments, the cap may be retained to the screw via adhesive material, which may consolidate and releasably hold the modular screw 30 and any cap embodiment together.

Figure 4A:
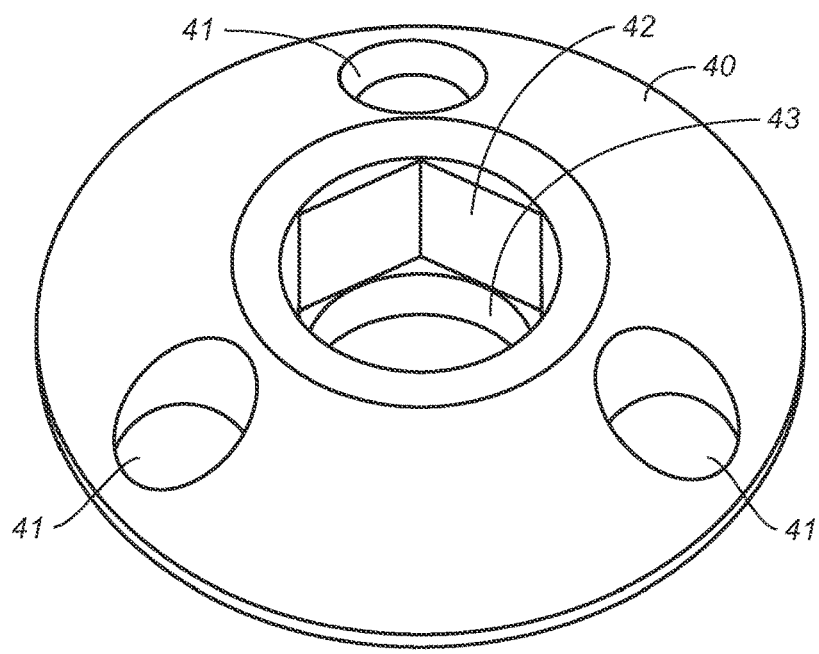
FIGS. 4A-4C illustrate a tenting cap (4A), a bone block fixation cap (4B), and a membrane fixation cap (4C), respectively, for affixation to the head region of the modular screw.
Figure 4B:
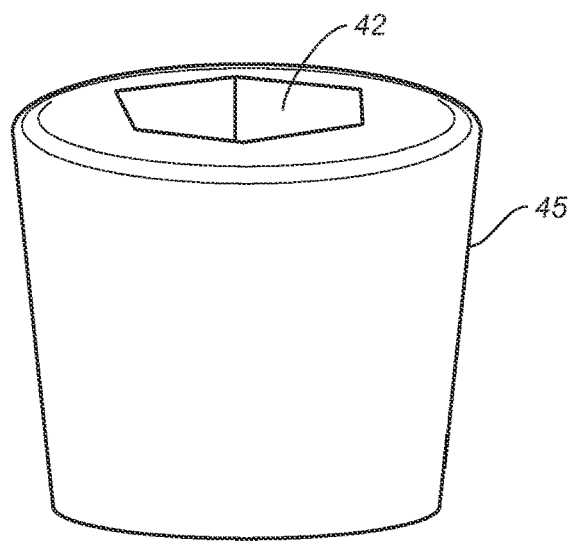
Figure 4C:
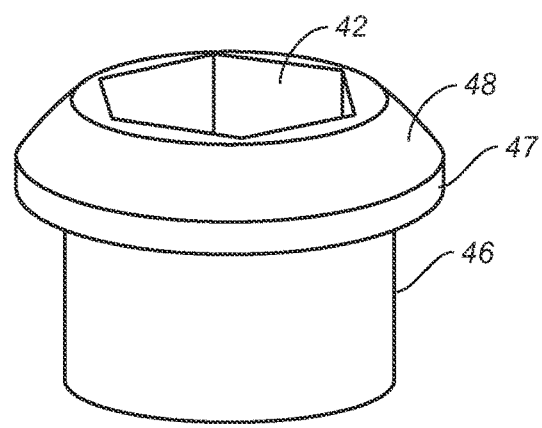

Referring to FIGS. 4A-4C, the tenting cap 40 of FIG. 4A encourages bone regeneration by creating a stable space around the screw assembly 1 and in which particulate graft material may be inserted. The tenting cap 40 of FIG. 4A is also used for fixation of barriers such as resorbable or non-resorbable membranes as well as for fixation of form-stable devices such as titanium mesh or plates.

Referring to FIG. 4A, a plurality of the eyelets 41 in tenting cap 40 are used for anchorage of soft tissues to bone. The surgeon passes sutures, or other wire or ligation methods, through the eyelets 41 to attach soft tissues, such as surgical flaps, periosteum, muscle, and fascia to bone. The advantage of this form of tissue fixation is that when a tissue flap is stabilized and attached to a modular screw 30 embedded in bone for example, by a suture traversing a portion of the tissue and the eyelets 41, the tissue can be placed in an optimal location and in a stable manner relative to the underlying bone. For example, when bone augmentation is performed, the tissue flap has to be mobilized to cover the large volume of graft placed over the bone. In this situation, simple suturing of the flap margins can cause too much tension of flap margins and risk wound dehiscence. By fixing the tissue about the upper surface of the tenting cap 40 of the embodiment of FIG. 4A, prior to attaching the tissue to the modular screw 30 via the eyelets 41, the tissue is placed in an optimal orientation based on the previous precise placement of the modular screw 30 at the target site, followed by securing the tenting cap 40 thereto, followed by tissue affixation.

As noted, a prime advantage of the invention is not only limited to dental applications, but is available anytime surgical screws are used to attach soft tissue to bone. Examples include repair of torn ligaments where the ligament is attached to bone, or when muscle attachment is severed from bone. The surgical screw assemblies of the invention can also be used to reattach muscle to underlying bone. Currently, conventional "suture anchors" are used for this application. However, with conventional suture anchors, the screw is placed first and the surgeon must then try to thread the screw with suture or wire while the screw is anchored on the patient, which may be very challenging. Alternatively, the surgeon can thread the screw first and then place the screw/thread. Both of these scenarios are very challenging for the surgeon. Using the embodiment of the present invention, the surgeon installs the modular screw 30 under optimal conditions with a much more efficient driver and without any suture attached during affixation of the suture anchor to bone. This is preferable and results in the ability to thread the suture in the tenting cap 41 prior to affixation to the body.

Another application is to connect two hard structures together. Examples of such application include inter-maxillary fixation, where following jaw surgery or trauma, it is desired to immobilize the maxilla and mandible by connecting these two structures together. This offers many advantages over current practice to pass wires in between maxillary and mandibular teeth to immobilize the jaws. Having the wires ligated to teeth has detrimental effects on teeth and the periodontium. The ability to use bone anchorage devices to ligate the jaws will provide a more stable connection, without having wires ligated to teeth.

Figure 5:
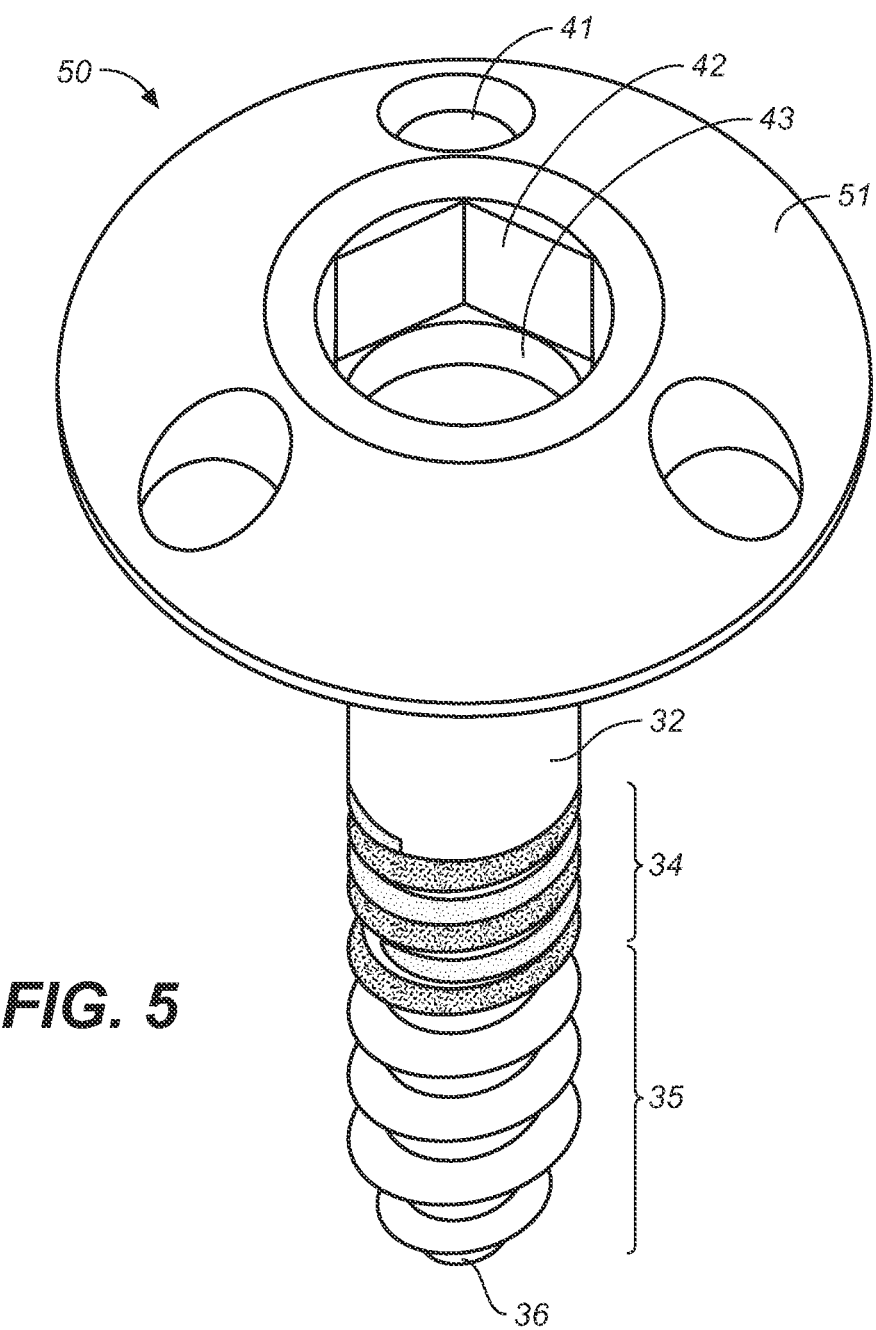
FIG. 5 illustrates a one-piece screw assembly of the invention.

Referring to FIG. 5, in one embodiment, the modular screw 50 is fabricated in a one-piece format. The one-piece screw 50 having a tenting cap 51 is comprised of threaded 33 and non-threaded 32 portions of the shaft 31. The threaded portion 33 is designed for bone anchorage. The threads include macrothreads 34 and microthreads 35 where the macrothreads 34 have larger and deeper pitch, while the microthreads 35 have thread pitches that are closer together and more shallow. The microthreads 35 are designed to increase primary stability of the screws, while reducing stress to bone during function that can lead to peri-implant crestal bone loss and eventual loss of function.

The mode of connection to the driver for insertion of the one-peace modular screw 50 is an internal hex fixture 42 centrally disposed within the upper surface of the tenting cap 51 and aligned with the axis of the axial length of the shaft 31 of the one-piece screw 50. Other modes of internal connection such as square, star or any other geometric shapes can be used for the connection between the driver and the hex fixture 42 of the modular screw 50. Also disposed within the interior of the hex fixture may be a stop 43 or abutment to prevent the mating portion of the hex fixture from misalignment or incorrect placement during rotational engagement of the driver with the hex fixture 42.

As will be appreciated by one of ordinary skill in the art the head portion of the one-piece unitary embodiment can be fabricated with any of the variety of head region or cap configurations, an example of which is FIG. 6 described below.

Figure 6:
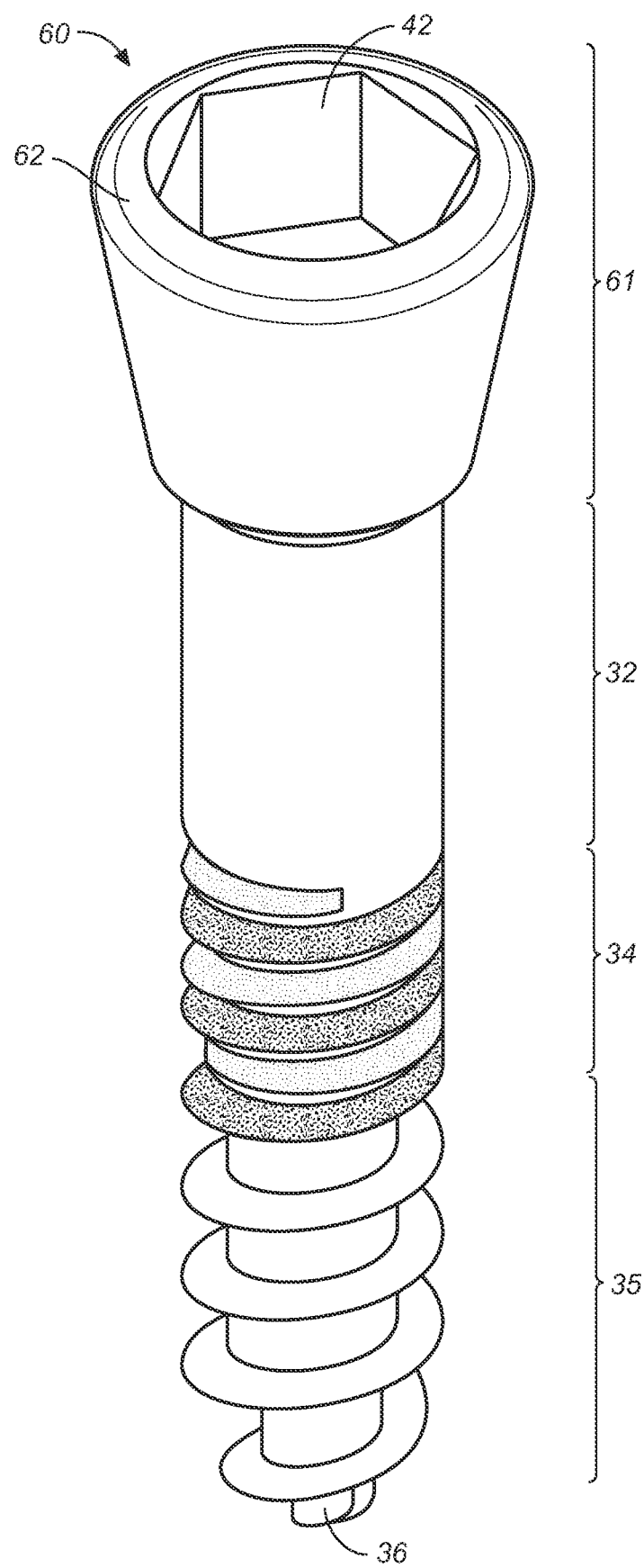
FIG. 6 is a block fixation screw assembly of the invention having a tapered head for applying compressive force along the lateral edge of the cap thereof.

Referring to FIG. 6, the block fixation screw 60 has a tapered head region 61. In preparation of the insertion of the modular screw 60, a countersink drill (not shown) with the same approximate dimensions as the diameter of a circumferential perimeter 62 of the tapered head 61 is used to create an osteotomy in the block graft. The block fixation screw 60 traverses the bone in a passive manner. The tapered head 61 of the block fixation screw 60 is tapered to apply compressive force along the lateral edge of the tapered head 61 and to the block graft to keep the graft engaged against host bone. The method of the present invention is placing a modular screw at a surgical site in use, the surgeon attaches the threaded base portion 1 at a target site by engaging the self-tapping threaded portion comprising tip 3 in the threaded portion 2 at the target site and driving the screw into the desired position into the bone. Advantageously, with a modular design of the present invention, the precise positioning of the base portion can be ascertained prior to the time that the head of the assembly is attached. As will be apparent from the embodiments described in FIGS. 1 and 2, the attachment of the threaded based portion 1 is more readily visualized without the screw head 2 being attached such that proper placement of the threaded base portion 1 is easily verified prior to attachment of the screw head. Once the proper placement of the base portion 1 is confirmed, then screw head 10 is attached in a discrete action to form the modular assembly at the target site.

While the present invention has been particularly shown and described with respect to certain preferred and illustrative embodiments, it will be understood by those skilled in the art that variations and modifications may be made therein without departing from the spirit and scope of the present invention.

I claim:

1. A method to place a surgical screw assembly comprising:
   placing a threaded base portion at a target surgical site by engaging a self-tapping portion comprising threaded portions along a length of a shaft and terminating in a distal tip, wherein the tip contacts the target surgical site and at least two contiguous portions are comprised of a region of microthreads and a region of macrothreads;
   attaching a head contiguous with a non-threaded portion and comprising means for engaging a driver to rotate the shaft around an axis of the length of the shaft;
   rotating a cap comprising an internal threaded portion about a most proximal portion of a threaded post integral with the length of the shaft,
   wherein a portion of the shaft and a driver mating fixture are disposed in an upper surface of the cap.

2. The method of claim 1, wherein the at least two contiguous threaded portions are both disposed along the axial length of the shaft between the non-threaded portion and the distal tip.

3. The method of claim 1, wherein a diameter of the shaft is between approximately 1.2-1.8 mm and the axial length of the shaft is between approximately 4 and 14 mm.

4. The method of claim 1, wherein the cap is a tenting cap having an internal hex nut rotated about the threaded post.

5. The method of claim 4, wherein the tenting cap is further comprised of an eyelet traversing an upper substantially planar surface of the tenting cap.

6. The method of claim 1, wherein the cap is a dome-shaped and is comprised of a plurality of eyelets traversing an upper substantially planar surface of the cap.

7. The method of claim 1, wherein the cap has a tapered outer edge along a vertical height thereof.

8. The method of claim 1, wherein the rotating step is comprised of engaging a driver mating fixture disposed in an upper surface of the cap.

* * * * *